US009820943B2

(12) United States Patent
Kapoor et al.

(10) Patent No.: US 9,820,943 B2
(45) Date of Patent: Nov. 21, 2017

(54) MICRONIZED AMOXICILLIN

(71) Applicant: DSM SINOCHEM PHARMACEUTICALS NETHERLANDS B.V., Delft (NL)

(72) Inventors: Rajinder Kapoor, Gurgaon (IN); Naresh Sharma, Gurgaon (IN); Neeraj Tewari, Echt (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 14/915,729

(22) PCT Filed: Sep. 1, 2014

(86) PCT No.: PCT/EP2014/068476
§ 371 (c)(1),
(2) Date: Mar. 1, 2016

(87) PCT Pub. No.: WO2015/032711
PCT Pub. Date: Mar. 12, 2015

(65) Prior Publication Data

US 2016/0199301 A1 Jul. 14, 2016

(30) Foreign Application Priority Data

Sep. 3, 2013 (IN) ........................... 2605/DEL/2013
Oct. 17, 2013 (EP) .................................... 13189124

(51) Int. Cl.
*A61K 9/14* (2006.01)
*A61K 31/43* (2006.01)
*C12P 37/04* (2006.01)
*C07D 499/00* (2006.01)

(52) U.S. Cl.
CPC ................ *A61K 9/14* (2013.01); *A61K 31/43* (2013.01); *C07D 499/00* (2013.01); *C12P 37/04* (2013.01)

(58) Field of Classification Search
CPC ........ A61K 9/14; A61K 31/43; C07D 499/00; C07D 37/04
See application file for complete search history.

(56) References Cited

U.S. PATENT DOCUMENTS 4,351,766 A * 9/1982 Walker .................. C07F 7/1896 540/312
2006/0166958 A1 7/2006 Groenendeel et al.
2011/0260063 A1* 10/2011 Huck ................ G01N 21/3563 250/340

FOREIGN PATENT DOCUMENTS

EP 1 808 166 7/2007
WO WO2004/082661 * 9/2004 ........... C07D 499/00

OTHER PUBLICATIONS

L.K.H. Bittner, et al, Near-Infrared Reflection Spectroscopy (NIRS) as a Successful Tool for Simultaneous Identification and Particle Size Determination of Amoxicillin Trihydrate, 54 J Pharm. Biomed. Anal. 1059 (2011).*

Graham Buckton & Anthony Beezer, the Relationship Between Particle Size and Solubility, 82 Intl. J Pharmaceut. R7 (1992).*

International Search Report for PCT/EP2014/067476, dated Sep. 29, 2014, 4 pages.

Written Opinion of the ISA for PCT/EP2014/067476, dated Sep. 29, 2014, 4 pages.

Bittner et al., "Near-infrared reflection spectroscopy (NIRS) as a successful tool for simultaneous identification and particle size determination of amoxicillin trihydrate", Journal of Pharmaceutical and Biomedical Analysis, vol. 54, 2011, pp. 1059-1064.

* cited by examiner

*Primary Examiner* — Sean M Basquill

(74) *Attorney, Agent, or Firm* — Sarika Singh; William D. Hare; McNeely, Hare & War, LLP

(57) ABSTRACT

The present invention relates to amoxicillin trihydrate compositions having a surface area of from 1.0 to 2.5 $m^2 \cdot g^{-1}$ that are free of organic contaminants such as dichloromethane, isopropanol, pivalic acid and triethyl amine and that have a purity of from 97.0% to 99.99%. Furthermore, the present invention relates to a method for the preparation of said amoxicillin trihydrate compositions and to the use of said compositions for the treatment of a bacterial infection.

20 Claims, 1 Drawing Sheet

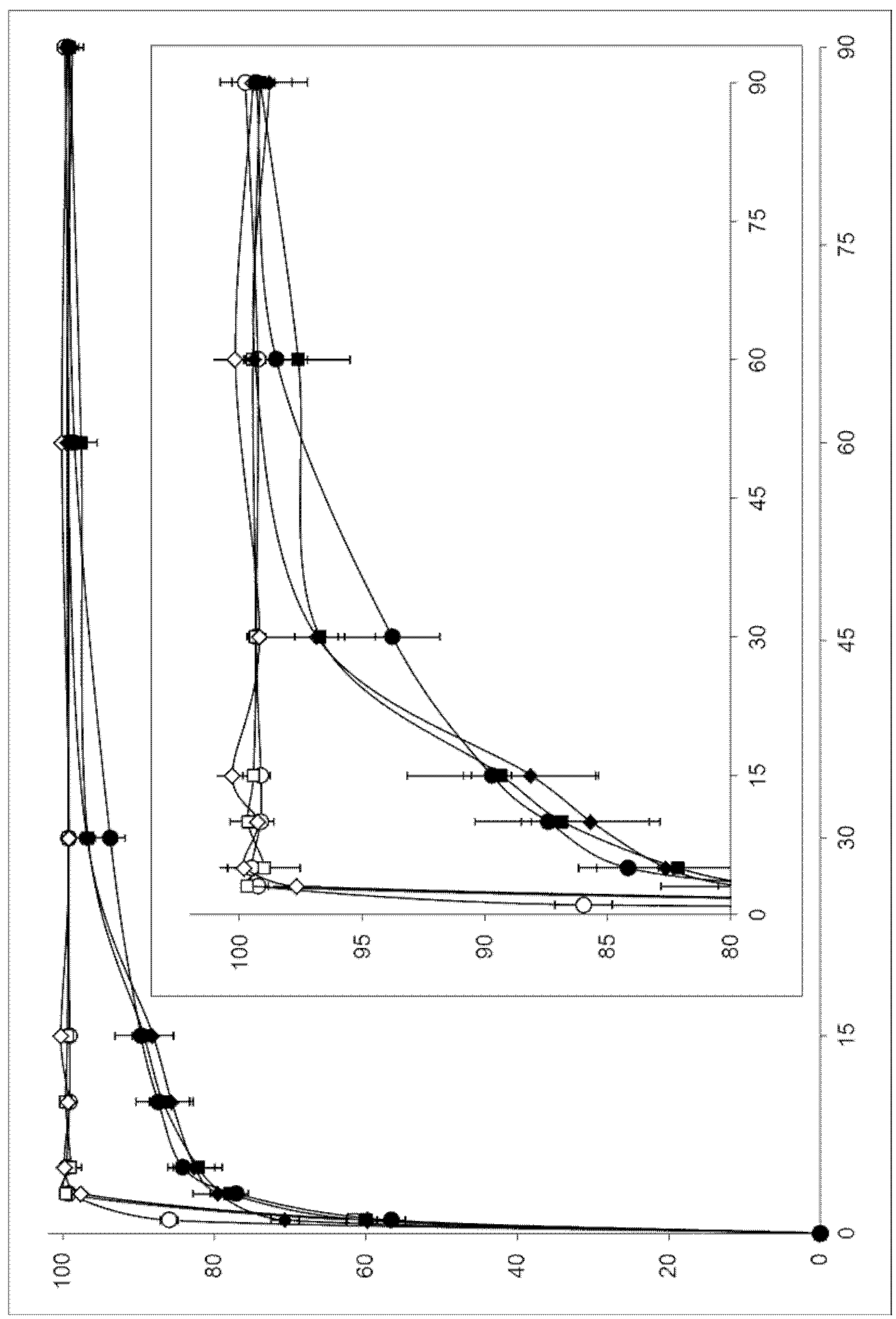
100
80
60
40
20
0
0
15
30
45
60
75
90
100
95
90
85
80

MICRONIZED AMOXICILLIN

This application is the U.S. national phase of International Application No. PCT/EP2014/068476 filed 1 Sep. 2014, which designated the U.S. and claims priority to EP Patent Application No. 13189124.4 filed 17 Oct. 2013, and IN Patent Application No. 2605/DEL/2013 filed 3 Sep. 2013, the entire contents of each of which are hereby incorporated by reference.

FIELD OF THE INVENTION

The present invention relates to amoxicillin trihydrate compositions having a surface area of from 1.0 to 2.5 $m^2 \cdot g^{-1}$ that are free of organic contaminants such as dichloromethane, isopropanol, pivalic acid and triethyl amine. Furthermore, the present invention relates to a method for the preparation of said amoxicillin trihydrate compositions and to the use of said compositions for the treatment of a bacterial infection.

BACKGROUND OF THE INVENTION

Amoxicillin is a well-known broad spectrum penicillin type antibiotic used for the treatment of both gram positive and gram negative bacterial infections in animals and humans. Most commonly, amoxicillin occurs as its trihydrate and this form, amoxicillin trihydrate, is predominantly used in formulations. For the purpose of the present invention, the term 'amoxicillin' therefore refers to amoxicillin trihydrate.

Traditionally, amoxicillin is prepared from penicillin G or penicillin V following complex chemical conversions involving the intermediate formation of 6-amino penicillanic acid, see for example J. Verweij et al. (*Recl. Trav. Chim. Pays-Bas* (1993) 112, 66-81 and references cited therein). There are various drawbacks associated with this approach, the main ones being the fact that such processes require hazardous and environmentally harmful chemicals. Such chemicals, mostly solvents such as butyl acetate, dichloromethane, dimethyl acetamide, isopropanol and/or pyridine and auxiliary chemicals such as pivalic acid and triethyl amine, end up as unwanted contaminants in the final product. Levels of residual solvents and auxiliary chemicals in amoxicillin are often significant and values for individual contaminants ranging from 300 to 2000 ppm are not unusual. A well-known contaminant such as dichloromethane may often occur in ranges of from 1000 to 5000 ppm.

Fortunately, in the last two decades major improvements have been realized with the introduction of environmentally benign enzyme-catalyzed processes that are carried out in water such as described in A. Bruggink et al. (*Org. Proc. Res. Dev.* (1998) 2, 128-133 and references cited therein).

Consequently, the majority of β-lactam antibiotics nowadays rarely contain organic solvents or hazardous auxiliary chemicals other than perhaps minute traces (less than 300 ppm) of harmless low-carbon alcohols such as ethanol or methanol. The foregoing is certainly also true for amoxicillin.

In contrast with the many and significant disadvantages of organic contaminants stands one advantage, namely the fact that contaminants usually have a positive effect on the extent to, and the rate at, which the major component, for example amoxicillin, dissolves in aqueous environment. This advantage stemming from traditional chemical synthesis of antibiotics has disappeared with the introduction of enzymatic processes leading to β-lactam antibiotics of markedly improved purity. And today there remains a drawback of enzymatically produced β-lactam antibiotics such as amoxicillin that requires to be solved, namely decreased (speed of) solubility.

DETAILED DESCRIPTION OF THE INVENTION

Confronted with the problem of reduced solubility of enzymatically produced amoxicillin trihydrate, tentatively resulting from the fact that enzymatically produced amoxicillin trihydrate generally is of higher purity than traditional chemically produced amoxicillin trihydrate, a solution to improve solubility was sought. Stated differently, an unexpected problem emerged in that as purity of enzymatically produced amoxicillin trihydrate increases, at the same time the solubility decreases. Reduction of particle size is a well-known approach to improve solubility. However, in the present invention it is in particular shown that by controlling the surface area between certain margins, amoxicillin trihydrate void of organic contaminants, can be tuned towards optimal solubility.

Thus, in a first aspect of the invention disclosed is a composition comprising from 97.0% to 99.99% (w/w) of amoxicillin trihydrate, having a surface area of from 1.0 to 2.5 m2·g−1, characterized in that it further comprises less than 500 ppm of a compound chosen from the list consisting of dichloromethane, isopropanol, pivalic acid and triethyl amine. Said low amounts of organic contaminants like dichloromethane, isopropanol, pivalic acid and triethyl amine typically distinguish the amoxicillin trihydrate of the present invention from that known from traditional chemical synthesis. A preferred surface area range is from 1.3 to 2.2 m2·g−1.

In one embodiment, the composition comprising amoxicillin trihydrate of the present invention preferably has an average particle size distribution wherein $D_{10}$ is from 1 μm to 3 μm, $D_{50}$ is from 5 μm to 15 μm, $D_{90}$ is from 15 μm to 30 μm and $D_{100}$ is from 30 μm to 100 μm. $D_{10}$ and $D_{50}$ values but also, to a lesser extent, $D_{90}$ and $D_{100}$ values are known parameters for indicating particle size distribution. The $D_{50}$ value refers to a particle size distribution such that 50% (v/v) of the particles has a particle size smaller than said value. The $D_{50}$ is also referred to as average volume-based grain size. Likewise, $D_{10}$ refers to the value for the particle size such that 10% (v/v) of the particles has a particle size smaller than said value. Similar definitions apply for $D_{90}$ and $D_{100}$. A still more preferred average particle size range is wherein $D_{10}$ is from 1.5 μm to 2.5 μm, $D_{90}$ is from 8 μm to 12 μm, $D_{90}$ is from 20 μm to 25 μm and $D_{100}$ is from 35 μm to 50 μm.

In another embodiment, the composition comprising amoxicillin trihydrate of the present invention may be distinguishable from traditional chemical amoxicillin by the presence of minute traces of protein, stemming from the biocatalyst used to produce said amoxicillin trihydrate. Thus, the amoxicillin trihydrate of the present invention comprises less than 500 ppm protein, preferably less than 250 ppm, more preferably less than 100 ppm protein. Following the enzymatic synthesis procedures as reported earlier in WO 2004/082661 or WO 2010/072765, combined with the micronization method of the second aspect of the present invention, the present invention even provides amoxicillin trihydrate comprising less than 50 ppm protein, i.e. from 2 to 35 ppm of protein.

In a preferred embodiment, the composition comprising amoxicillin trihydrate of the present invention is highly pure and thus suitable for use in medical treatment. Preferably, the amoxicillin trihydrate of the present invention has a purity of from 96.0% to 100%, more preferably of from 97.0% to 99.99%, most preferably from 98.0% to 99.95%, still most preferably of from 98.5% to 99.9%. Samples of the amoxicillin trihydrate of the present invention have purities of 99.4±0.5%, preferably of 99.4±0.4%, routinely of 99.4±0.3%. As a consequence, not only does the amoxicillin trihydrate comprise unprecedented low amounts of impurities known from traditional chemical synthesis, it is also virtually free of any other contaminants. In the context of the present invention, purity of amoxicillin trihydrate is defined as 100%*((amount of amoxicillin trihydrate [MW 419.45] in g)/(amount of sample in g)).

Surprisingly, and contradictory to expectations, the enzymatically prepared amoxicillin trihydrate of the present invention displayed decreased rather than increased dissolution when tested according to the United States Pharmacopoeia (USP) paddle method. The rationale behind this observation is at present unknown. With this observation at hand, a further surprising observation is that the amoxicillin trihydrate of the present invention appears to display improved efficacy in the application for the treatment of bacterial infections, notably in veterinary applications. In contrast with the results of the USP paddle method, it is established in the present invention that the amoxicillin trihydrate of the present invention forms clear solutions under standard application conditions using tap water more rapidly than non-micronized amoxicillin trihydrate. Measurement of the contact angle of both non-micronized amoxicillin and the amoxicillin trihydrate of the present invention reveals that the latter product has a higher contact angle, namely from 80-130, preferably from 90-120, more preferably from 95-115. There is however no unambiguous theory how this explains the unexpected observations made.

The amoxicillin trihydrate composition of the present invention displays improved efficacy with respect to their congeners prior to grinding, micronization or pulverization. Due to the improved solubility profile, dry syrups dissolve faster so that they may be administered faster. But also, and even more importantly, the constituents of tablets comprising the amoxicillin trihydrate composition of the present invention that are taken orally also dissolve faster in the body fluid such as that of the stomach. As a consequence a larger percentage of the active ingredient is available earlier to perform its pharmaceutical function.

In a second aspect, the present invention provides a method for the preparation of a composition comprising amoxicillin trihydrate according to the first aspect of the invention comprising the steps of:

(a) Contacting 6-aminopenicillanic acid and an ester or an amide of D-4-hydroxyphenylglycine or a salt thereof together with an enzyme in water;
(b) Isolating and drying solid amoxicillin trihydrate formed in step (a);
(c) Reducing the particle size of the solid amoxicillin trihydrate obtained after step (b).

In one embodiment the ester or amide of D-4-hydroxyphenylglycine is D-4-hydroxyphenylglycine ethyl ester or D-4-hydroxyphenylglycine methyl ester or D-4-hydroxyphenylglycine hydroxyethyl ester.

In another embodiment said reducing of the particle size is effected by micronization, for example using a jet mill.

In yet another embodiment said enzyme is an enzyme capable of catalyzing the synthesis or hydrolysis of amoxicillin such as, for example a penicillin acylase (or penicillin amidase) or an α-aminoacid ester hydrolase. Preferably said enzyme is immobilized on a carrier material that is inert to the reaction conditions and facilitates removal of the enzyme biocatalyst after the formation of amoxicillin trihydrate.

In a third aspect, the present invention provides a pharmaceutical composition comprising the composition comprising amoxicillin trihydrate of the first aspect for use in the treatment of a bacterial infection.

In one embodiment said use is particularly suitable for veterinary purposes. For example the amoxicillin trihydrate of the first aspect of the invention is used for making feed pellets. Production of feed pellets is normally performed at relatively high temperatures ranging from 70 to 130° C., preferably from 80 to 120° C. The production of feed pellets using traditional chemically produced amoxicillin has a major disadvantage, namely that when small (micronized) particles of this traditional chemically produced amoxicillin are used these particles display rapid disintegration as a result of the elevated temperature. In feed pellet production this drawback is resolved by adding excess traditional chemically produced amoxicillin, even up to 30% excess, so that the overall result is that the required amount of active pharmaceutical ingredient in the pellet is achieved by applying excess active pharmaceutical ingredient and allowing the presence of significant amounts of unwanted degradation products. Surprisingly, the amoxicillin trihydrate of the present invention does not display the above mentioned disintegration, has a much higher stability and can consequently be applied in much lower amounts in the production of feed pellets.

In another embodiment the amoxicillin trihydrate composition of the present invention may advantageously be used for the preparation by wet granulation of tablets comprising amoxicillin and tablets comprising amoxicillin and a β-lactamase inhibitor, examples of which are clavulanic acid, sulbactam and tazobactam or salts thereof. A preferred β-lactamase inhibitor is clavulanic acid or a pharmaceutically acceptable salt thereof. The advantage of the amoxicillin trihydrate composition of the present invention is the fact that dimensions are similar to those commonly available for other tablet constituents. Such compatibility leads to improved uniformity of blends and resulting granules and tablets which in turn also improves the amoxicillin dissolution profile. The same advantage stemming from uniformity in different particle sizes also applies to the use of the amoxicillin trihydrate composition of the present invention in amoxicillin comprising dry syrups. Here too formulations with improved solubility, suspendability and uniformity are the result.

LEGEND TO THE FIGURES

FIG. 1 displays the dissolution profiles of amoxicillin trihydrate samples, determined according to the dissolution analysis protocol given in the General section of the Examples. X-axis: time in minutes; Y-axis: percentage amoxicillin released in solution. The insert depicts a zoomed portion of the percent amoxicillin released from 80 to 100%. Error bars indicate the standard deviation (SD).

The following symbols are used (see also Table 1 in Example 1):

○ Non-micronized amoxicillin powder sample 1
□ Non-micronized amoxicillin powder sample 2
◇ Non-micronized amoxicillin powder sample 3
● Micronized amoxicillin powder sample 4 (obtained from non-micronized amoxicillin powder sample 1)
■ Micronized amoxicillin powder sample 5 (obtained from non-micronized amoxicillin powder sample 2)

♦ Micronized amoxicillin powder sample 6 (obtained from non-micronized amoxicillin powder sample 3)

EXAMPLES

General

Amoxicillin trihydrate was prepared enzymatically according to known procedures such as described in WO 2004/082661 or WO 2010/072765.

Residual solvents dichloromethane, isopropanol and triethyl amine were determined by head space gas chromatography using a Perkin Elmer Model Autosystem consisting of a Flame Ionisation detector (FID), a headspace autosampler model HS 40 and TOWS v 6.2.0 software. Sample vials for the autosampler where 50 mL injection vials with a crimp cap with PTFE-coated butyl rubber septum.

Gas Chromatograph:

Column: Varian CP-SIL 5CB 30 m×0.25 mm ID, df=0.25 μm

Oven temperature: 70° C.

Detector temperature: 220° C.

Detector sensitivity (range): 1

Attenuation: 16

Injector temperature: 220° C.

Carrier gas: Nitrogen

Carrier flow rate: 9.0 psi

Hydrogen flow rate: 40-45 mL·min$^{-1}$

Zero air: 400-446 mL·min$^{-1}$

Split flow: 20 mL·min$^{-1}$

Autosampler:

Sample temperature: 70° C.

Needle temperature: 70° C.

Transfer temperature: 90° C.

Inject time: 0.06 min

Thermostating time: 20 min

Withdrawal time: 0.1 min

Pressurization time: 0.5 min

GC cycle time: 15 min

Residual pivalic acid was determined by gas chromatography using a Perkin Elmer Model Autosystem 'XL' consisting of a Flame Ionisation detector (FID) and TOWS v 6.2.0 software. Sample vials for the autosampler where 50 mL injection vials with a crimp cap with PTFE-coated butyl rubber septum.

Gas Chromatograph:

| | | |
|---|---|---|
| Column: | Varian CP-SIL 5CB 50 m × 0.53 mm ID, df = 5.0 μm | |
| Oven temperature: | 150° C.: | 3 min |
| | 150° C. → 200° C.: | ramp rate 15° C. · min$^{-1}$ |
| | 200° C.: | 10 min |
| | Equilibrium time: | 0.2 min |
| Detector temperature: | 240° C. | |
| Detector sensitivity (range): | 1 | |
| Attenuation: | 16 | |
| Injector temperature: | 225° C. | |
| Carrier gas: | Nitrogen | |
| Carrier flow rate: | 6.5 psi | |
| Hydrogen flow rate: | 40-45 mL · min$^{-1}$ | |
| Zero air: | 404-446 mL · min$^{-1}$ | |
| Inject volume: | 5.0 μL | |
| Split flow: | 65 ± 5 mL · min$^{-1}$ | |

Particle size distribution values $D_{10}$, $D_{50}$, $D_{90}$ and $D_{100}$ were determined using laser diffraction applying Malvern equipment. A suitable apparatus for determining $D_{10}$, $D_{50}$, $D_{90}$ and $D_{100}$ is a Malvern particle sizer 2600 C or a Malvern Zeta Sizer.

Specific powder surface area was determined using nitrogen gas sorption (Smartsorb, Smart Instruments, Mumbai, India). Prior to measurements, samples were regenerated by degassing to remove moisture and contamination. The regenerated sample was dipped in liquid nitrogen and the quantity of the adsorbed gas was measured using a thermal conductivity detector and subsequently integrated using an electronic circuit in terms of counts. The instrument was calibrated by injecting a known quantity of nitrogen. The measured parameters were subsequently used to calculate the surface area of the sample by employing the adsorption theories of Brunauer, Emmett and Teller (BET).

Dissolution analysis of amoxicillin trihydrate powder samples was carried out using the USP/NF paddle method at a rotational speed of 75 rpm. Ultrapure ELGA laboratory water (900 mL) was used as dissolution medium. Media were equilibrated to 37.0±0.5° C. prior to dissolution. Amoxicillin trihydrate sample powder (500 mg) was directly added to the dissolution apparatus (Electrolab USP-24, India). Samples were collected at 0, 1, 3, 5, 10, 15, 30, 60 and 90 min, filtered through 0.2 μm filters and analyzed by HPLC. Dissolution profiles were constructed by plotting the percentage amoxicillin released against time.

The HPLC system (Shimadzu Corporation, Kyoto, Japan) comprised of an SCL-10A VP system controller, LC-10AT VP liquid chromatograph, FCV-10AL VP flow control valve, DGU-14A degasser, SIL-10AD VP auto-injector, CTO-10AS VP column oven, SPD-M20A prominence diode array (PDA) detector and data acquisition Class-VP 6.10 software. The HPLC method was adopted from the United States Pharmacopoeia (USP). The method was validated for linearity, precision, accuracy and intra- and inter-day variability. The mobile phase was 50 mM monobasic potassium phosphate:methanol (96:4, v/v, pH 5.0). All analyses were carried out using Lichrospher® 100 RP-18e analytical column (5 μm, Merck KGaA, Darmstadt, Germany) under isocratic conditions at a flow rate of 1.0 mL·min$^{-1}$ at 25° C. with 20 μL injection volume. Effluent was monitored at a wavelength of 230 nm. Samples for calibration curve generation were prepared in 50 mM monobasic potassium phosphate:methanol 1:1 (v/v) proportion at a concentration range of 1 to 600 μg·mL$^{-1}$.

Contact angles of amoxicillin trihydrate powder samples were measured by the sessile drop method using an Drop Shape Analyzer instrument (FTA 1000, First Ten Angstrom, Virginia, USA). Powder samples were mounted on double sided adhesive tape adhered to a glass slide and excess powder was removed by tapping the slide. A drop of probe liquid (water) was dispersed onto the sample surface and video images were captured by the FTA image analyzer. The contact angle was calculated by the instrument by fitting a mathematical expression to the shape of the drop followed by calculating the slope of the tangent to the drop at the liquid-solid-vapor interface line. The surface tension of ultrapure ELGA laboratory water was measured to be 73±0.5 mN·m$^{-1}$ at 25° C. All measurements were performed in air under ambient conditions and an average of four measurements was reported in the below Examples.

Example 1

Micronization of Amoxicillin Trihydrate

Three different batches of enzymatically prepared amoxicillin trihydrate were micronized in a jet mill micronizer with a capacity of 50-150 kg·h$^{-1}$. Micronization involves high speed particle collision thus creating increasingly smaller fines through particle-on-particle impact. Centrifugal force holds larger particles in grinding area while centripetal force drives fines towards the center for discharge. On stream product was fed through a feeding chamber for intended micronization. A suitable recipe based on Augar speed, primary and secondary air was put on auto mode to initiate the micronization process. Qualified compressed air was used as primary and secondary air. Multiple recipes were a result of experimental trials taken during the Performance Qualification (PQ) phase to generate a design space.

TABLE 1

Characteristics of micronized and non-micronized amoxicillin

| | | Surface Area ($m^2 \cdot g^{-1}$) Mean ± SD | Average Particle Size (μm) | | | | Contact Angle Mean ± SD |
|---|---|---|---|---|---|---|---|
| | | (n = 3) | $D_{10}$ | $D_{50}$ | $D_{90}$ | $D_{100}$ | (n = 4) |
| 1 | Non-micronized | 0.58 ± 0.09 | 12.3 | 39.8 | 93.3 | 275.9 | 75.50 ± 2.95 |
| 2 | Non-micronized | 0.69 ± 0.03 | 13.5 | 40.6 | 94.3 | 237.5 | 67.70 ± 1.39 |
| 3 | Non-micronized | 0.72 ± 0.16 | 13.1 | 39.3 | 91.7 | 230.1 | 71.54 ± 1.08 |
| 4 | Micronized 1 | 1.78 ± 0.03 | 1.9 | 10.1 | 23.1 | 44.6 | 110.68 ± 0.23 |
| 5 | Micronized 2 | 2.03 ± 0.15 | 1.9 | 10.0 | 22.5 | 44.3 | 97.89 ± 1.22 |
| 6 | Micronized 3 | 1.69 ± 0.07 | 1.9 | 10.0 | 22.4 | 38.9 | 107.84 ± 1.72 |

Parameters operated were:
- Augar Speed: 5-90 rpm
- Primary Air Pressure: 2-8 kg·cm$^{-2}$
- Secondary Air Pressure: 4-10 kg·cm$^{-2}$ The surface area (in triplicate), average particle size and contact angle (in quadruplicate) were determined as outlined in the General section. The purity of the amoxicillin trihydrate samples was 99.4±0.3% and were void of dichloromethane, isopropanol, pivalic acid and triethyl amine. Other results are summarized in Table 1.

Example 2

Powder Dissolution of Micronized and Non-Micronized Amoxicillin Trihydrate (Dissolution Apparatus Electrolab USP-24)

The three non-micronized (i.e. entries 1-3 of Table 1) and micronized (i.e. entries 4-6 of Table 1) amoxicillin trihydrate samples of Example 1 were subjected to a powder dissolution test (in triplicate) as outlined in the General section. The results are graphically displayed in FIG. 1 and Tables 2 to 7.

TABLE 2

Dissolution data for non-micronized amoxicillin (entry 1 of Table 1)

| Time | Amoxicillin released in solution (%) | | | | |
|---|---|---|---|---|---|
| (min) | #1 | #2 | #3 | Mean | SD |
| 0 | 0 | 0 | 0 | 0 | 0 |
| 1 | 84.65 | 86.65 | 86.65 | 85.98 | 1.16 |
| 3 | 99.74 | 99.01 | 99.01 | 99.25 | 0.42 |
| 5 | 99.44 | 99.54 | 99.54 | 99.51 | 0.06 |
| 10 | 98.65 | 99.04 | 99.73 | 99.14 | 0.55 |
| 15 | 99.28 | 98.69 | 99.38 | 99.12 | 0.37 |
| 30 | 99.50 | 99.56 | 98.87 | 99.31 | 0.38 |
| 60 | 99.56 | 99.10 | 99.10 | 99.25 | 0.27 |
| 90 | 99.93 | 99.61 | 99.74 | 99.76 | 0.16 |

TABLE 3

Dissolution data for non-micronized amoxicillin (entry 2 of Table 1)

| Time | Amoxicillin released in solution (%) | | | | |
|---|---|---|---|---|---|
| (min) | #1 | #2 | #3 | Mean | SD |
| 0 | 0 | 0 | 0 | 0 | 0 |
| 1 | 61.68 | 61.21 | 62.23 | 61.71 | 0.51 |
| 3 | 99.58 | 99.88 | 99.60 | 99.69 | 0.17 |
| 5 | 99.89 | 99.79 | 97.29 | 98.99 | 1.47 |
| 10 | 99.66 | 98.95 | 100.36 | 99.66 | 0.71 |
| 15 | 99.51 | 98.98 | 99.80 | 99.43 | 0.42 |
| 30 | 99.65 | 99.00 | 99.34 | 99.33 | 0.32 |
| 60 | 99.56 | 99.17 | 99.60 | 99.45 | 0.24 |
| 90 | 99.24 | 99.24 | 98.96 | 99.15 | 0.17 |

TABLE 4

Dissolution data for non-micronized amoxicillin (entry 3 of Table 1)

| Time | Amoxicillin released in solution (%) | | | | |
|---|---|---|---|---|---|
| (min) | #1 | #2 | #3 | Mean | SD |
| 0 | 0 | 0 | 0 | 0 | 0 |
| 1 | 57.32 | 60.63 | 61.23 | 59.73 | 2.10 |
| 3 | 96.94 | 97.25 | 98.77 | 97.65 | 0.98 |
| 5 | 99.68 | 100.87 | 98.80 | 99.78 | 1.03 |
| 10 | 99.06 | 99.42 | 99.27 | 99.25 | 0.18 |
| 15 | 100.69 | 100.64 | 99.55 | 100.29 | 0.64 |
| 30 | 99.21 | 99.18 | 99.14 | 99.18 | 0.04 |
| 60 | 99.14 | 100.41 | 100.92 | 100.16 | 0.92 |
| 90 | 99.58 | 99.28 | 99.46 | 99.44 | 0.15 |

TABLE 5

Dissolution data for micronized amoxicillin (entry 4 of Table 1)

| Time | Amoxicillin released in solution (%) | | | | |
|---|---|---|---|---|---|
| (min) | #1 | #2 | #3 | Mean | SD |
| 0 | 0 | 0 | 0 | 0 | 0 |
| 1 | 54.49 | 57.74 | 57.67 | 56.64 | 1.85 |
| 3 | 76.32 | 76.89 | 78.12 | 77.11 | 0.92 |
| 5 | 85.25 | 82.78 | 84.47 | 84.17 | 1.26 |
| 10 | 88.15 | 86.80 | 87.34 | 87.43 | 0.68 |
| 15 | 90.61 | 89.05 | 89.49 | 89.71 | 0.81 |
| 30 | 93.27 | 95.75 | 91.85 | 93.77 | 1.95 |
| 60 | 97.15 | 99.70 | 98.65 | 98.50 | 1.28 |
| 90 | 97.76 | 99.52 | 100.66 | 99.31 | 1.46 |

TABLE 6

| Dissolution data for micronized amoxicillin (entry 5 of Table 1) | | | | | |
|---|---|---|---|---|---|
| Time | Amoxicillin released in solution (%) | | | | |
| (min) | #1 | #2 | #3 | Mean | SD |
| 0 | 0 | 0 | 0 | 0 | 0 |
| 1 | 58.56 | 62.91 | 58.32 | 59.93 | 2.58 |
| 3 | 78.61 | 80.12 | 75.20 | 77.98 | 2.52 |
| 5 | 83.91 | 82.77 | 79.73 | 82.14 | 2.16 |
| 10 | 89.18 | 88.59 | 82.76 | 86.84 | 3.55 |
| 15 | 90.98 | 92.05 | 84.94 | 89.32 | 3.84 |
| 30 | 94.78 | 99.20 | 96.17 | 96.72 | 2.26 |
| 60 | 97.29 | 99.86 | 95.65 | 97.60 | 2.12 |
| 90 | 99.33 | 99.64 | 98.47 | 99.15 | 0.61 |

TABLE 7

| Dissolution data for micronized amoxicillin (entry 6 of Table 1) | | | | | |
|---|---|---|---|---|---|
| Time | Amoxicillin released in solution (%) | | | | |
| (min) | #1 | #2 | #3 | Mean | SD |
| 0 | 0 | 0 | 0 | 0 | 0 |
| 1 | 70.98 | 72.37 | 68.67 | 70.68 | 1.87 |
| 3 | 82.73 | 76.25 | 79.68 | 79.56 | 3.24 |
| 5 | 84.40 | 78.46 | 84.94 | 82.60 | 3.59 |
| 10 | 85.63 | 82.85 | 88.53 | 85.67 | 2.84 |
| 15 | 87.94 | 85.45 | 90.95 | 88.11 | 2.76 |
| 30 | 96.08 | 96.66 | 97.81 | 96.85 | 0.88 |
| 60 | 99.56 | 98.85 | 99.69 | 99.37 | 0.45 |
| 90 | 97.01 | 99.48 | 99.78 | 98.76 | 1.52 |

Example 3

Powder Dissolution of Micronized and Non-Micronized Amoxicillin Trihydrate (Visual Determination of Clarity)

Non-micronized amoxicillin trihydrate (3.0 g) was added to a 2 L beaker and drinking water (1000 mL) was added. The mixture was stirred for 2 min at 300±10 rpm at 30±1° C. After two minutes the stirrer was stopped. The same procedure was applied to a sample of micronized amoxicillin trihydrate. Both mixtures were visually observed. The non-micronized sample appeared cloudy whereas the micronized sample appeared clear.

The invention claimed is:

1. A composition comprising:

(i) from 97.0% to 99.99% (w/w) of amoxicillin trihydrate having a surface area of from 1.0 to 2.5 $m^2 \cdot g^{-1}$ having an average particle size distribution of $D_{10}$ from 1 μm to 3 μm, $D_{50}$ from 5 μm to 15 μm, $D_{90}$ from 15 μm to 30 μm, and $D_{100}$ from 30 μm to 100 μm, and less than 500 ppm of at least one compound selected from the group consisting of dichloromethane, isopropanol, pivalic acid and triethyl amine.

2. The composition according to claim 1, wherein the surface area of the amoxicillin trihydrate is from 1.3 to 2.2 $m^2 \cdot g^{-1}$.

3. The composition according to claim 2, wherein the composition has an average particle size distribution of $D_{10}$ from 1.5 μm to 2.5 μm, $D_{50}$ from 8 μm to 12 μm, $D_{90}$ from 20 μm to 25 μm and $D_{100}$ from 35 μm to 50 μm.

4. The composition according to claim 1, wherein the composition comprises from 2 to 35 ppm of protein.

5. The composition according to claim 1, wherein the amoxicillin trihydrate has a purity of 99.4±0.5%.

6. A method for the preparation of a composition according to claim 1, wherein the method comprises the steps of:

(a) contacting 6-aminopenicillanic acid and an ester or an amide of D-4-hydroxyphenylglycine or a salt thereof together with an enzyme in water;

(b) isolating, and drying solid amoxicillin trihydrate formed in step (a); and (c) reducing the particle size of the solid amoxicillin trihydrate obtained after step (b).

7. The method according to claim 6, wherein step (c) comprises reducing the particle size of the solid amoxicillin trihydrate by micronization.

8. The method according to claim 6, wherein the enzyme is a penicillin acylase or an α-amino acid ester hydrolase.

9. A method for the treatment of a bacterial infection comprising administering to a subject in need thereof an effective amount of the composition according to claim 1.

10. The method according to claim 9, wherein the composition is a veterinary composition.

11. A pharmaceutical composition comprising the amoxicillin trihydrate of claim 1.

12. The pharmaceutical composition of claim 11, wherein the pharmaceutical composition further comprises a β-lactamase inhibitor.

13. The pharmaceutical composition of claim 1, wherein the β-lactamase inhibitor comprises one or more of clavulanic acid, sulbactam and tazobactam.

14. The pharmaceutical composition of claim 11, wherein the pharmaceutical composition is prepared by wet granulation.

15. The pharmaceutical composition of claim 11, wherein the pharmaceutical composition comprises a tablet.

16. The composition according to claim 1, wherein the composition comprises less than 500 ppm of protein.

17. The composition according to claim 1, wherein the composition comprises less than 50 ppm of protein.

18. The composition according to claim 1, Wherein the amoxicillin trihydrate has been synthesized in an enzymatic process.

19. The composition according to claim 1, wherein the amoxicillin trihydrate has a contact angle from 80-130.

20. A composition comprising:

(iii) from 97.0% to 99.99% (w/w) of amoxicillin trihydrate having a surface area of from 1.0 to 2.5 $m^2 \cdot g^{-1}$ having an average particle size distribution of $D_{10}$ from 1 μm to 3 μm, $D_{50}$ from 5 μm to 15 μm, $D_{90}$ from 15 μm to 30 μm and $D_{100}$ from 30 μm to 100 μm, and (iv) less than 500 ppm of at least one compound selected from the group consisting of dichloromethane, isopropanol, pivalic acid and triethyl amine, wherein the composition has a purity of 99.4±0.5%, a contact angle from 80-130, and less than 500 ppm of protein.

* * * * *